US007767700B2

(12) United States Patent
Bradford

(10) Patent No.: US 7,767,700 B2
(45) Date of Patent: *Aug. 3, 2010

(54) METHOD OF PROVIDING PIRFENIDONE THERAPY TO A PATIENT

(75) Inventor: Williamson Ziegler Bradford, Ross, CA (US)

(73) Assignee: Intermune, Inc., Brisbane, CA (US)

( * ) Notice: Subject to any disclaimer, the term of this patent is extended or adjusted under 35 U.S.C. 154(b) by 470 days.

This patent is subject to a terminal disclaimer.

(21) Appl. No.: 11/959,338

(22) Filed: Dec. 18, 2007

(65) Prior Publication Data

US 2008/0194644 A1  Aug. 14, 2008

Related U.S. Application Data

(60) Provisional application No. 60/870,593, filed on Dec. 18, 2006.

(51) Int. Cl.
  *A61K 31/44*  (2006.01)
(52) U.S. Cl. .......................... 514/350; 514/345
(58) Field of Classification Search .................. None
  See application file for complete search history.

(56) References Cited

U.S. PATENT DOCUMENTS

| | | | |
|---|---|---|---|
| 6,956,044 B1 | 10/2005 | Margolin | |
| 7,407,973 B2 | 8/2008 | Ozes et al. | |
| 7,413,749 B2 | 8/2008 | Wright et al. | |
| 2004/0048902 A1 | 3/2004 | Kiyonaka et al. | |
| 2006/0110358 A1 | 5/2006 | Hsu et al. | |
| 2007/0053877 A1 | 3/2007 | Crager et al. | |
| 2007/0054842 A1 | 3/2007 | Blatt et al. | |
| 2007/0092488 A1 | 4/2007 | Strieter et al. | |
| 2007/0117841 A1 | 5/2007 | Ozes et al. | |
| 2007/0172446 A1 | 7/2007 | Blatt et al. | |
| 2007/0203202 A1 | 8/2007 | Robinson et al. | |
| 2008/0003635 A1 | 1/2008 | Ozes et al. | |
| 2008/0019942 A1 | 1/2008 | Seiwert et al. | |
| 2008/0025986 A1 | 1/2008 | Ozes et al. | |
| 2008/0161361 A1 | 7/2008 | Wu et al. | |
| 2008/0194644 A1 | 8/2008 | Bradford | |
| 2008/0287508 A1 | 11/2008 | Robinson et al. | |
| 2009/0016967 A1 | 1/2009 | Schnapp et al. | |

FOREIGN PATENT DOCUMENTS

WO  WO-2007/038315  4/2007
WO  WO-2007/064738  6/2007

OTHER PUBLICATIONS

Angulo et al., Pirfenidone in the treatment of primary sclerosing cholangitis. *Digest. Dis. Sci.* 47(1): 157-161 (2002).
Babovic-Vuksanovic et al., Phase I trial of pirfenidone in children with neurofibromatosis 1 and plexiform neurofibromas. *Pediatric Neurol.* 36(5): 293-300 (2007).
Cho et al., Pirfenidone slows renal function decline in patients with focal segmental glomerulosclerosis. *Clin. J. Am. Soc. Nephrol.* 2: 906-913 (2007).
Davies et al., Idiopathic pulmonary fibrosis current and future treatment options. *Am. J. Respir. Med.* 1(3): 211-224 (2002).
GNI Pharma Corporate News Letter, GNI's F647 shows positive results in phase II human clinical trial of idiopathic pulmonary fibrosis, Jun. 18, 2008.
Lasky et al., Pirfenidone. *IDrugs.* 7(2):166-172 (2004).
Oku et al., Antifibrotic action of pirfenidone and prednisolone: Different effects on pulmonary cytokines and growth factors in bleomycin-induced murine pulmonary fibrosis. *Eur. J. Pharmacol.* 590: 400-408 (2008).
Pirespa® package insert, Shionogi & Co., Ltd. Prepared in Oct. 2008 (version 1). English-language translation.
Printout from web link "http://www.nfincmn.org/Sept 2001 vol. 2 No. 2.pdf" which appears on its face to be a derivative form of "NF Flash newsletter vol. 1 No. 2 (2001)" and includes article Babovic-Vuksanovic, Clinical trial on pirfenidone. (publication date unknown); web link was known to be active Sep. 2008.
Raghu et al., Treatment of idiopathic pulmonary fibrosis with a new antifibrotic agent, pirfenidone. *Am. J. Respir. Crit. Care Med.* 159: 1061-1069 (1999).
Simone et al., Oral pirfenidone in patients with chronic fibrosis resulting from radiotherapy: a pilot study. *Radiation Oncol.* 2: 19-24 (2007).
Walker et al., Pirfenidone for chronic progressive multiple sclerosis. *Mult. Scler.* 7: 305-312 (2001).

(Continued)

*Primary Examiner*—Brian-Yong S Kwon
*Assistant Examiner*—Bong-Sook Baek
(74) *Attorney, Agent, or Firm*—Marshall, Gerstein & Borun LLP; John A. Bendrick

(57) ABSTRACT

The invention relates to methods for decreasing adverse events associated with pirfenidone (5-methyl-1-phenyl-2-(1H)-pyridone) therapy. The invention discloses an optimized dose escalation scheme that results in the patient having increased tolerance to adverse events associated with the administration of pirfenidone. The invention also discloses a starter pack that may be used in conjunction with the dose escalation scheme.

19 Claims, 7 Drawing Sheets

OTHER PUBLICATIONS

Welch et al., Power Point slides from InterMune, Inc. Capacity Results Conference Call. Innovative Medicines for Pulmonology and Hepatology, Feb. 3, 2009.

Communication pursuant to Article 94(3) EPC from counterpart application EP 07 865 831.7, Apr. 16, 2010 (6 pages).

Azuma et al., Double-blind, placebo-controlled trial of pirfenidone in patients with idiopathic pulmonary fibrosis. 171: 1040-7 (2005).

Babovic-Vuksanovic et al., Phase II trial of pirfenidone in adults with neurofibromatosis type 1. *Neurology*. 67: 1860-2 (2006).

Bowen et al., Open-label study of pirfenidone in patients with progessive forms of multiplesclerosis. *Mult.Scler* . 9: 280-3 (2003).

Cain et al., Inhabition of tumor necrosis factor and subsequent endotoxin shock by pirfenidone. *Int. J. lmmunopharmacol*. 20: 685-95 (1998).

Zhang et al., Pirfenidone reduces fibronectin synthesis by cultured human retinal pigment epithelial cells. *Aust. N Z J Opthalmol*. 26: S74-6 (1998).

PCT Search Report for PCT/US2007/087988 dated Apr. 28, 2008.

PCT Written Opinion for PCT/US2007/087988 dated Apr. 28, 2008.

Food and Drug Administration Center for Drug Evaluation and Research, Pulmonary-Allergy Drugs Advisory Committee (PADAC) Meeting Transcript (Tuesday, Mar. 9, 2010), published at http://www.fda.gov/downloads/AdvisoryCommittees/CommitteesMeetingMaterials/Drugs/Pulmonary-AllergyDrugsAdvisoryCommittee/UCM208806.pdf.

Pirfenidone NDA 22-535 Pulmonary-Allergy Drugs Advisory Committee Mar. 9, 2010, slide deck (InterMune, Inc.), published at http://www.fda.gov/downloads/AdvisoryCommittees/CommitteesMeetingMaterials/Drugs/Pulmonary-AllergyDrugsAdvisoryCommittee/UCM206399.pdf.

Pulmonary-Allergy Drugs Advisory Committee Meeting, Pirfenidone Capsules, NDA 22-535, S-000, Mar. 9, 2010, slide deck (U.S. Food and Drug Administration), published at http://www.fda.gov/downloads/AdvisoryCommittees/CommitteesMeetingMaterials/Drugs/Pulmonary-AllergyDrugsAdvisoryCommittee/UCM206398.pdf.

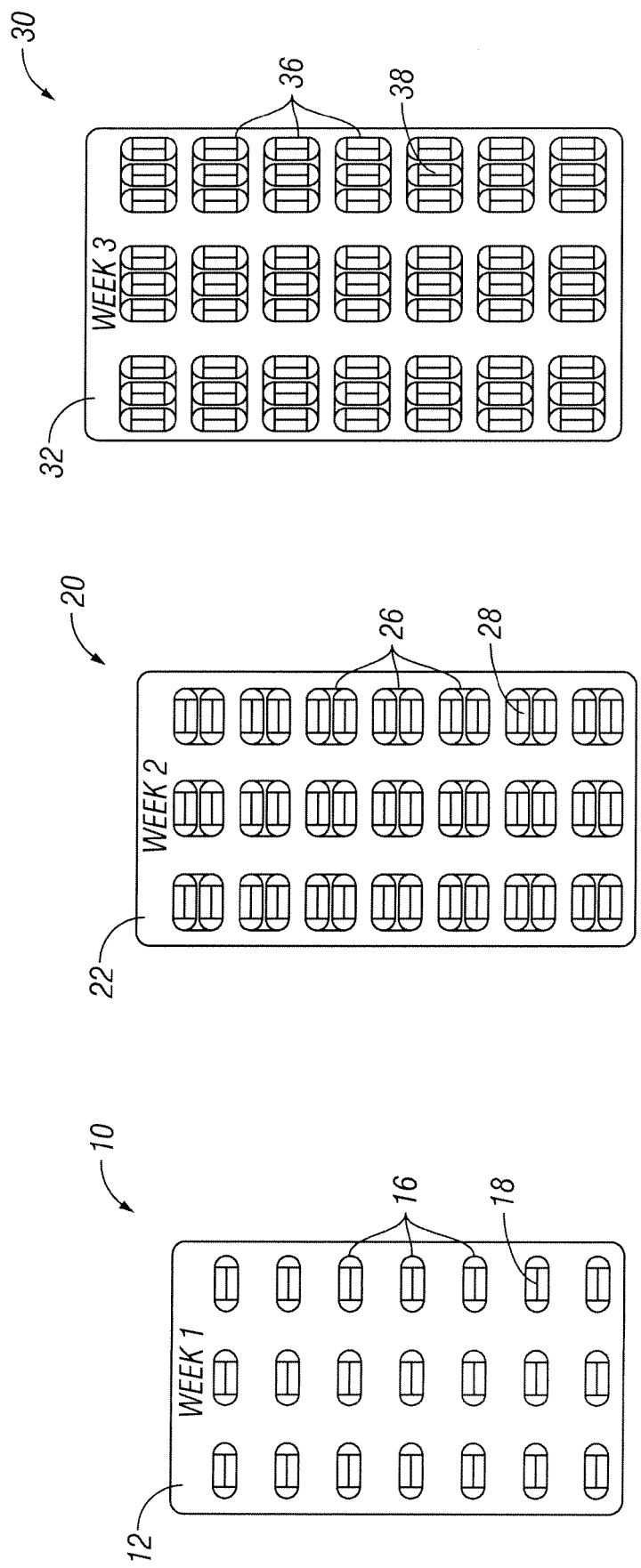

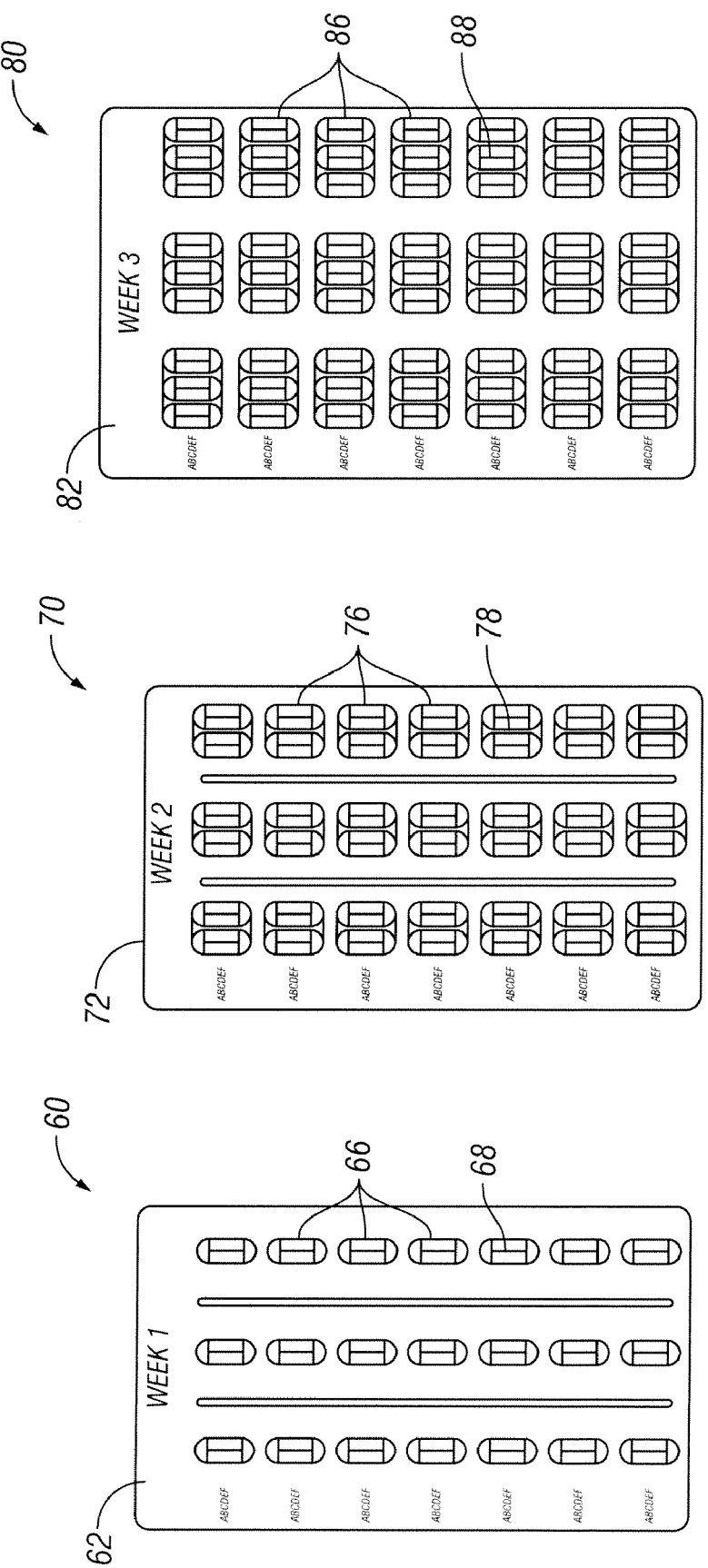

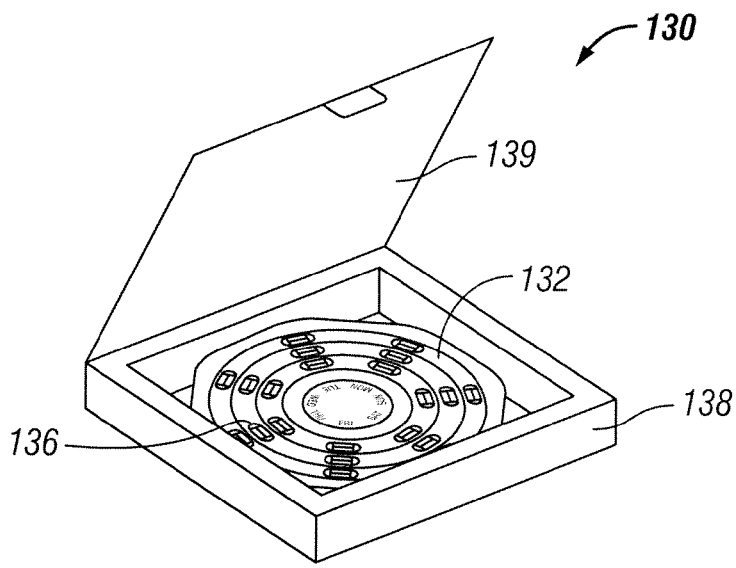
FIG. 13
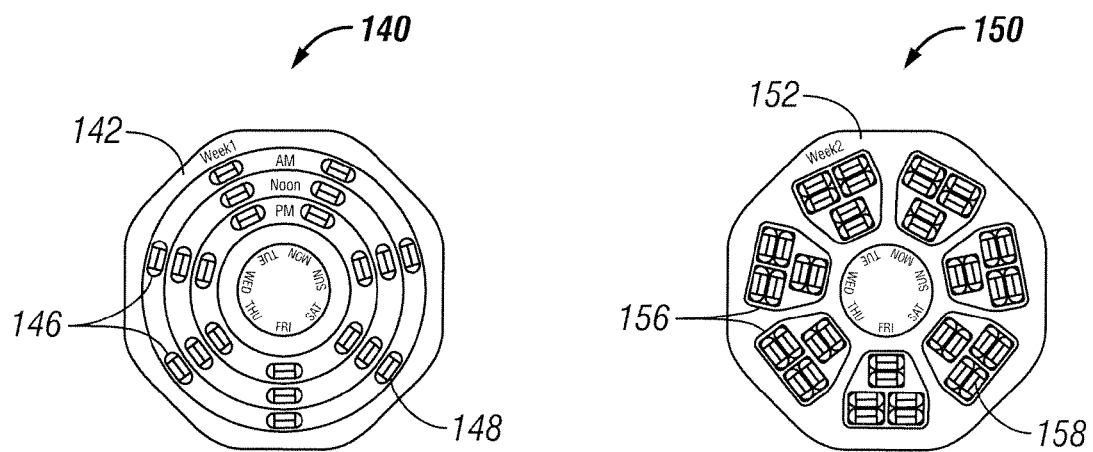
FIG. 14
FIG. 15
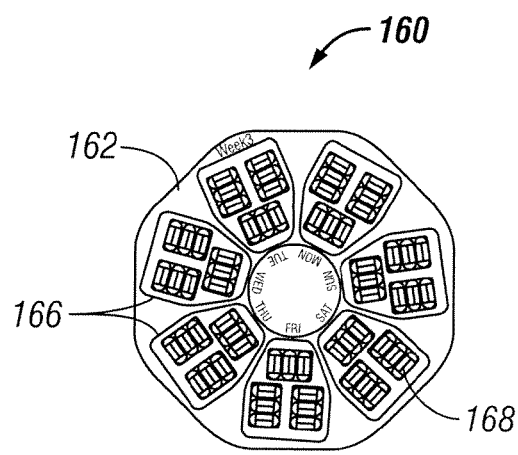
FIG. 16

METHOD OF PROVIDING PIRFENIDONE THERAPY TO A PATIENT

CROSS REFERENCE TO RELATED APPLICATIONS

This application claims the benefit of U.S. Provisional Application Ser. No. 60/870,593, filed Dec. 18, 2006, the disclosure of which is incorporated by reference in its entirety.

BACKGROUND

1. Field of the Invention

The invention relates to methods for decreasing adverse events associated with pirfenidone (5-methyl-1-phenyl-2-(1H)-pyridone) therapy.

2. Description of the Related Art

Pirfenidone is small drug molecule whose chemical name is 5-methyl-1-phenyl-2-(1H)-pyridone. It is a non-peptide synthetic molecule with a molecular weight of 185.23 Daltons. Its chemical elements are expressed as $C_{12}H_{11}NO$, and its structure and synthesis are known. Pirfenidone is manufactured commercially and being evaluated clinically as a broad-spectrum anti-fibrotic drug. Several pirfenidone Investigational New Drug Applications (INDs) are currently on file with the U.S. Food and Drug Administration. Phase II human investigations are ongoing or have recently been completed for pulmonary fibrosis, renal glomerulosclerosis, and liver cirrhosis. There have been other Phase II studies that used pirfenidone to treat benign prostate hypertrophy, hypertrophic scarring (keloids), and rheumatoid arthritis.

Pirfenidone is being investigated for therapeutic benefits to patients suffering from fibrosis conditions such as Hermansky-Pudlak Syndrome (HPS) associated pulmonary fibrosis and idiopathic pulmonary fibrosis (IPF). Pirfenidone is also being investigated for a pharmacologic ability to prevent or remove excessive scar tissue found in fibrosis associated with injured tissues including that of lungs, skin, joints, kidneys, prostate glands, and livers. Published and unpublished basic and clinical research suggests that pirfenidone may safely slow or inhibit the progressive enlargement of fibrotic lesions, and prevent formation of new fibrotic lesions following tissue injuries.

It is understood that one mechanism by which pirfenidone exerts its therapeutic effects is modulating cytokine actions. Pirfenidone is a potent inhibitor of fibrogenic cytokines and TNF-$\alpha$. It is well documented that pirfenidone inhibits excessive biosynthesis or release of various fibrogenic cytokines such as TGF-$\beta$1, bFGF, PDGF, and EGF. Zhang S et al., *Australian and New England J Opthalmology* 26:S74-S76 (1998). Experimental reports also show that pirfenidone blocks the synthesis and release of excessive amounts of TNF-$\alpha$ from macrophages and other cells. Cain et al., *Int'l J Immunopharmacology* 20:685-695 (1998).

As an investigational drug, pirfenidone is provided in tablet and capsule forms principally for oral administration. Various formulations have been tested and adopted in clinical trials and other research and experiments. The most common adverse reactions or events associated with pirfenidone therapy include gastrointestinal upset, nausea, fatigue, somnolence, dizziness, headache, and photosensitivity rash. Many of these effects can interfere with everyday activities and quality of life. These effects appear to be dose related. The adverse reactions associated with pirfenidone therapy are exacerbated when pirfenidone is administered at these higher doses.

Currently, adverse events following administration of pirfenidone are alleviated by dose reduction or discontinuation of pirfenidone. In a recent study, for adverse events rated Grade 2 or worse, the dosage was reduced in a stepwise manner: from 9 tablets having 200 mg of pirfenidone per day to 6 tablets having 200 mg of pirfenidone per day and 6 tablets having 200 mg of pirfenidone per day to 3 tablets having 200 mg of pirfenidone per day. Azuma, A. et al., *Am J Respir Crit. Care Med* 171:1040-47 (2005) ("Azuma study"). More specifically, if, after a period of 14 days of observation with reduced dosage, the adverse event persisted or increased, the dosage was further reduced by one more step—from 6 tablets per day to 3 tablets per day. If the adverse event persisted or increased despite reducing the dosage to 3 tablets per day, the study medication was discontinued.

The Azuma study discloses a dose-titration schedule for all patients wherein patients received a 200-mg dose of pirfenidone three times a day for the first two days; then a 400-mg dose of pirfenidone three times a day for the following two days; and then a maximum 600-mg dose of pirfenidone three times a day for the remainder of treatment. Thus, the maximum dose obtained by the Azuma study was only 1,800 mg/day of pirfenidone. Additionally, the dose-titration schedule of the Azuma study reaches the full maximum dosage of pirfenidone after only four days of treatment. There is significant reason to believe that the Azuma dose escalation does not optimally match the rate of dose escalation with the rate at which a patient develops sufficient tolerance to reduce the incidence of adverse events. Thus, there remains an unmet clinical need for a method of administering higher doses of pirfenidone to a patient in a manner that eliminates or minimizes adverse events, such as nausea, vomiting, gastrointestinal upset, drowsiness, dizziness, headache, somnolence, and other undesirable side effects.

SUMMARY

The present invention overcomes the unmet clinical need by providing an improved, optimized dose escalation scheme for the administration of pirfenidone. The dose escalation scheme of the present invention provides pirfenidone in an amount such that the full maximum dosage is not reached for at least one week. In a preferred embodiment, the full maximum dosage of pirfenidone is not reached until about Day 15 of treatment. The method of the present invention allows for a maximum dosage of 2,403 mg of pirfenidone per day to be administered to a patient and also reduces the incidence of adverse events associated with the administration of pirfenidone by more accurately matching dose escalation with tolerance development in the patient. Indeed, it has been observed that even as the dosage escalates using the dosing escalation scheme described herein, adverse events, such as somnolence, decrease.

The present invention discloses a method of providing pirfenidone therapy to a patient comprising providing an initial daily dosage of pirfenidone to the patient in a first amount for the duration of a first period of time; providing a second daily dosage of pirfenidone to the patient in a second amount for a second period of time; and providing a final daily dosage of pirfenidone to the patient in a final amount for a final period of time, wherein the first and second periods of time together total at least about 7 days, more preferably about 8, 9, 10, 11 or 12 days, and most preferably about 13 or 14 days. In some embodiments, the first and second periods can together total up to about 15 or about 20 or 21 days.

In one embodiment, the first amount is about 801 mg/day; the second amount is about 1,602 mg/day; and the third amount is about 2,403 mg/day. In another embodiment, the first period of time is about 7 days; the second period of time is about 7 days; and the third period of time is in the range of about 1 day up to an unlimited number of days. In specific embodiments, the third period of time lasts at least about 1 month, at least about 2 months, at least about 3 months, at least about a year, at least about 18 months, at least about 2 years, or more than 2 years, at least about 3 years, at least about 4 years, at least about 5 years, or as long as therapy with pirfenidone is needed.

The present invention also discloses a starter pack comprising dosage amounts of pirfenidone and compartments that separate the dosage amounts according to a daily dosage of pirfenidone. Advantageously, the compartments can be arranged in columns and in rows, although other arrangements are also contemplated.

In one exemplary embodiment, the starter pack comprises rows designating Day numbers and separate columns for the number of times a dosage of pirfenidone is taken each day. In one embodiment, the starter pack may comprise separate rows for Days 1, 2, 3, 4, 5, 6, 7, 8, 9, 10, 11, 12, 13, and 14 with three separate columns for three dosage amounts to be taken each day. In one embodiment, each of the three compartments for Days 1, 2, 3, 4, 5, 6, and 7 separately contain one pill of 267-mg pirfenidone and each of the three compartments for Days 8, 9, 10, 11, 12, 13, and 14 separately contain two pills of 267-mg pirfenidone. In another embodiment, each week of treatment may be designated on a separate panel. In another embodiment, each panel contained within the starter pack may be approximately the same size. In another embodiment, the starter pack has compartments arranged such that a user of the starter pack may administer the pirfenidone in accordance with the dose escalation method taught by the present invention.

Also contemplated is use of pirfenidone in preparation of a medicament for the treatment of a fibrosis condition comprising administration of pirfenidone according to a dosing regimen as disclosed herein.

BRIEF DESCRIPTION OF THE DRAWINGS

FIG. 1 shows a structure of a portion of a starter pack for the first week of treatment.

FIG. 2 shows a structure of a portion of a starter pack for the second week of treatment.

FIG. 3 shows a structure of a portion of a starter pack for the third week of treatment.

FIG. 6 shows another structure of a portion of a starter pack for the first week of treatment.

FIG. 7 shows another structure of a portion of a starter pack for the second week of treatment.

FIG. 8 shows another structure of a portion of a starter pack for the third week of treatment.

FIG. 13 shows a starter pack having a casing material holding at least one circular panel containing pirfenidone.

FIG. 14 shows another structure of a portion of a circular starter pack for the first week of treatment.

FIG. 15 shows another structure of a portion of a circular starter pack for the second week of treatment.

FIG. 16 shows another structure of a portion of a circular starter pack for the third week of treatment.

DETAILED DESCRIPTION

Figure 4:
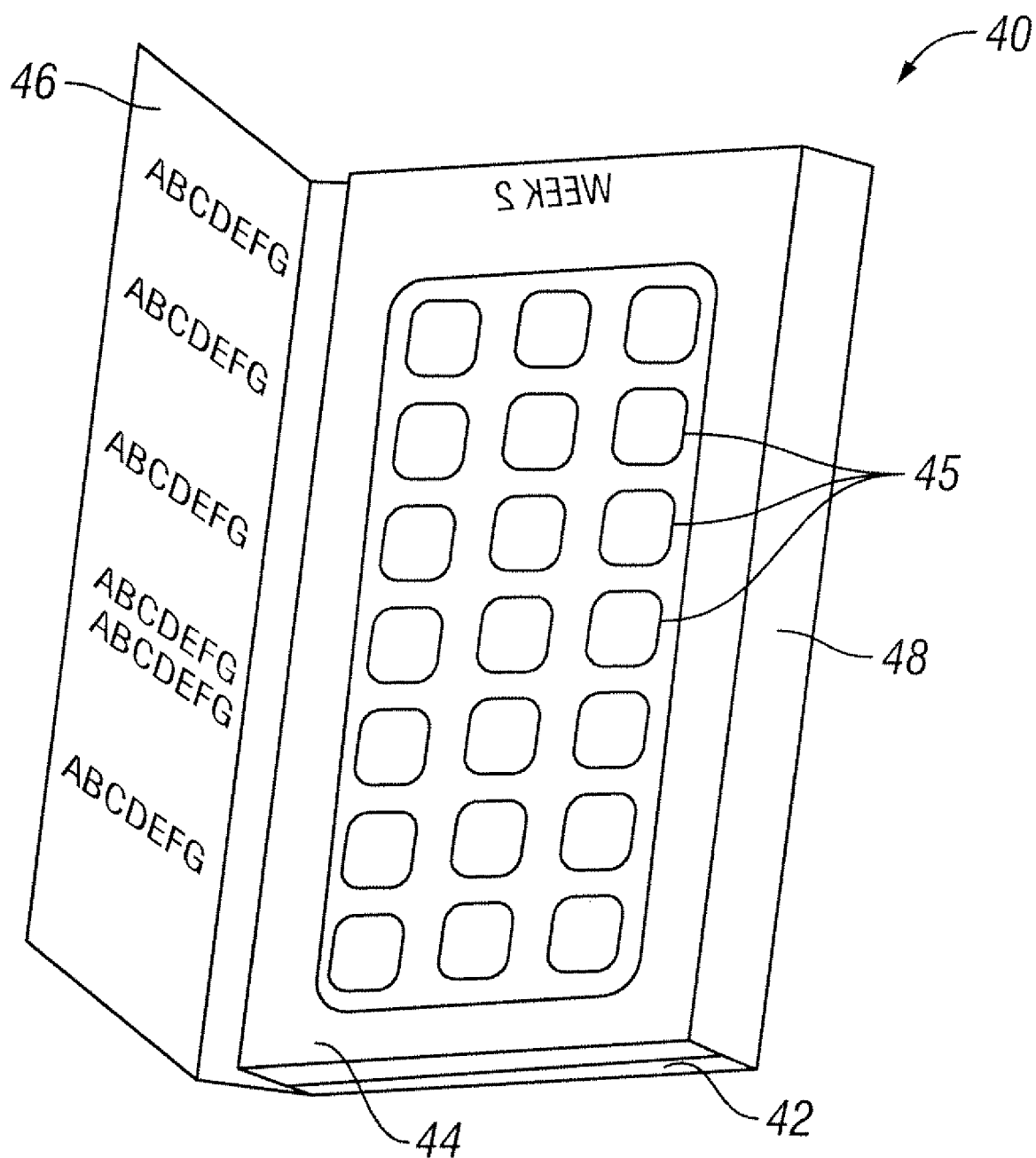
FIG. 4 shows a starter pack having multiple panels that are folded.

The present invention discloses a method of providing pirfenidone therapy to a patient with an escalating dosage regimen that mitigates adverse events associated with the use of pirfenidone and, it is believed, better matches the development of tolerance to potentially adverse effects of the drug with increases in the dosage. In one embodiment of the present invention is a method of providing pirfenidone therapy to a patient comprising providing an initial daily dosage of pirfenidone to the patient in a first amount for the duration of a first period of time; providing a second daily dosage of pirfenidone to the patient in a second amount for a second period of time; and providing a final daily dosage of pirfenidone to the patient in a final amount for a final period of time. The sum of the first and second periods of time is preferably at least about 7 days, more preferably about 8, 9, 10, 11, or 12 days, and most preferably about 13 or 14 days. In some embodiments, the first and second periods can together total up to about 15 or about 20 or 21 days. Although it is also contemplated that the first and second periods together can total more than 21 days, and can (for example) be 22, 24, 26, or 30 days, it is believed that the longer dose escalation periods are less than optimal, due to the decrease in therapeutic benefit to the patient resulting from the delay in administering the full therapeutic dosage.

Although the present disclosure exemplifies dose escalation regimens having three steps, it is also possible to have more steps in the same amount of time, so that the dosage escalates in smaller steps. Indeed, if desired, each dose can be incrementally larger than the previous dose, or the dose can escalate every day, every two days, or every three or four days, for example. Regardless of the dose escalation step size, the use of an initial dose and an ending dose in the amounts discussed below is particularly preferred.

In one embodiment, the first amount is in the range of about 400 mg/day to about 1,200 mg/day. In another embodiment, the first amount is in the range of about 700 mg/day to about 900 mg/day. In another embodiment, the first amount is in the range of about 780 mg/day to about 820 mg/day. In another embodiment, the first amount is about 801 mg/day.

In one embodiment, the second amount is in the range of about 1,200 mg/day to about 2,000 mg/day. In another embodiment, the second amount is in the range of about 1,500 mg/day to about 1,700 mg/day. In another embodiment, the second amount is in the range of about 1,580 mg/day to about 1,620 mg/day. In another embodiment, the second amount is about 1,602 mg/day.

In one embodiment, the third amount is in the range of about 2,000 mg/day to about 3,000 mg/day. In another embodiment, the third amount is in the range of about 2,300 mg/day to about 2,400 mg/day. In another embodiment, the third amount is in the range of about 2,380 mg/day to about 2,420 mg/day. In another embodiment, the third amount is about 2,403 mg/day.

In one embodiment, the first period of time is in the range of about 3 days to about 10 days. In another embodiment, the first period of time is about 6 to about 8 days. In another embodiment, the first period of time is about 7 days.

In one embodiment, the second period of time is in the range of about 3 days to about 10 days. In another embodiment, the second period of time is about 6 to about 8 days. In another embodiment, the second period of time is about 7 days.

In one embodiment, the final period of time is in the range of about 1 day to an unlimited number of days. Preferably, the final period of time will be however long the duration of treatment with pirfenidone should last.

In one embodiment of the present invention is a method of providing pirfenidone therapy to a patient comprising providing an initial daily dosage of pirfenidone to the patient in an amount of 801 mg/day over the course of Day 1 to Day 7; providing a second daily dosage of pirfenidone to the patient in an amount of 1602 mg/day over the course of Day 8 to Day 14; and providing a final daily dosage of pirfenidone to the patient in an amount of 2403 mg/day on the beginning of Day 15 and continuing with the 2403 mg/day dosage on each day following Day 15.

In one embodiment, the patient is administered one capsule (a sub-daily dosage) comprising 267-mg of pirfenidone three times a day over the course of Day 1 to Day 7, to provide a daily dosage of 801 mg pirfenidone; then the patient is administered two capsules (a sub-daily dosage) comprising 267-mg of pirfenidone three times a day over the course of Day 8 to Day 14, to provide a daily dosage of 1602 mg pirfenidone; and then the patient is administered three capsules (a sub-daily dosage) comprising 267-mg of pirfenidone three times a day on Day 15 and each day thereafter, to provide a daily dosage of 2403 mg pirfenidone where the therapy continues after Day 15.

In one embodiment, a dosage amount of pirfenidone is taken with food. In another embodiment, the patient is instructed to administer the dosage of pirfenidone with food.

In another embodiment of the present invention, there is provided a starter pack comprising pirfenidone. Starter packs are a relatively easy method for singulating, transporting, storing and finally dispensing oral solid drugs. Such packs include, for instance, a planar transparent piece of plastic provided with "blisters" or convex protrusions configured in rows and columns. Each of the blisters or convex protrusions is sized to receive a singulated dosage amount of the particular oral solid drug being dispensed.

Typically, at least one backing layer is fastened to a solid receiving side of the blister pack. This layer is a low strength retaining barrier. This low strength retaining layer stretches across the backs of the blisters and retains the singulated oral dosage amounts individually sealed within each of the blisters.

Dispensing of drugs from such blister packs is easy to understand. The consumer presses down on a blister from the convex side of the blister. Such pressure bears directly against the singulated oral dosage amount contained in the blister. The singulated oral solid drug is then forced through the low strength retaining barrier. This low strength retaining barrier at least partially tears and breaks away. During this partial breaking and tearing away, the singulated oral dosage amount is partially—but typically not totally—ejected from its individual blister. Preferably, it is during this partial ejection that the oral solid drug is grasped by the user and consumed as directed. The result is a safe, sterile dispensing of the drug in desired single dosage amounts from the blister pack.

The starter pack of the present invention may comprise various dosage amounts of pirfenidone designated within blisters or other individual compartments so that the patient will take the proper dosage amount of the drug each day. The starter pack may comprise many different forms. One embodiment of the starter pack is shown in FIGS. 1-3. FIG. 1 shows a portion of a starter pack comprising dosage amounts for the first week of therapy using pirfenidone. The starter pack (10) for the first week of treatment may comprise a panel (12) having a plurality of compartments (16) for containing a dosage amount (18) of pirfenidone. The compartments (16) may be arranged in column and row fashion as illustrated, although other arrangements are also contemplated, including having all of the compartments arranged in a line, or having them arranged in a circular fashion. In an embodiment where the starter pack comprises columns and rows, each daily dosage may be represented in a singular row or a singular column.

FIG. 2 shows a portion of a starter pack comprising dosage amounts for the second week of therapy using pirfenidone. The starter pack (20) for the second week of treatment may comprise a panel (22) having a plurality of compartments (26) for containing a dosage amount (28) of pirfenidone. The compartments (26) for the second week of treatment may be fashioned to hold a greater amount of pirfenidone than the compartments (16) for the first week of treatment. The dosage amount (28) of pirfenidone for the second week may be greater than the dosage amount (18) of the first week.

FIG. 3 shows a portion of a starter pack comprising dosage amounts for the third week of therapy using pirfenidone. The starter pack (30) for the third week of treatment may comprise a panel (32) having a plurality of compartments (36) for containing a dosage amount (38) of pirfenidone. The compartments (36) for the third week of treatment may be fashioned to hold a greater amount of pirfenidone than the compartments (26) for the second week of treatment. The dosage amount (38) of pirfenidone for the third week may be greater than the dosage amount (28) of the second week.

Although FIGS. 1-3 show a starter pack wherein a panel represents one week of dosages, it is contemplated that a panel may be constructed to comprise more or less compartments. For instance, a panel may be constructed to hold dosage amounts for three days of treatment. In another embodiment, a panel may be constructed to hold dosage amounts for six days of treatment. In another embodiment, a panel may be constructed to hold dosage amounts for ten days of treatment. Any number of days and dosages in a single panel are contemplated by the inventors. Preferably, the starter pack may be designed so that the user administers pirfenidone according to the dose escalation scheme of the present invention.

In one embodiment, the starter pack comprises panels giving dosage amounts of pirfenidone for the first week of treatment and the second week of treatment. In another embodiment, the starter pack further comprises a panel giving dosage amounts of pirfenidone for the third week of treatment. In another embodiment, the starter pack comprises a panel or an insert that gives instructions to a patient for administering the proper dosage amount of pirfenidone.

In one embodiment, the starter pack may comprise only dosage amounts for the first week of treatment and the second week of treatment. Preferably, such a starter pack may also comprise instructions to the patient for administering the pirfenidone from a bottle for therapy after dose escalation is completed. It is contemplated that the user of the starter pack will continue therapy with pirfenidone pills from a bottle after dose escalation is completed.

The size of the starter pack and the panels that comprise the starter pack may be typical of similar starter packs already known. In a preferred embodiment, each panel within a starter pack is approximately of similar size dimensions as the other panels of the starter pack.

In some embodiments, the starter pack comprises a unitary structure, wherein the unitary structure comprises more than one panel and each panel may comprise dosage amounts for one week of treatment. In some embodiments, the starter pack comprises a panel that has printed instructions thereon. FIG. 4 shows a starter pack (40) having multiple panels (42, 44, 46) that are folded. The starter pack has at least one region (48) capable of folding so that the separate panels (42, 44, 46) can be stacked upon one another while the starter pack (40) maintains its unitary structure. In some embodiments, the starter pack may comprise panels (42, 44) having compartments for containing dosages of pirfenidone. The dosages may be pushed through the low strength retaining barrier at points (45) opposite the location of the blisters.

Figure 5:
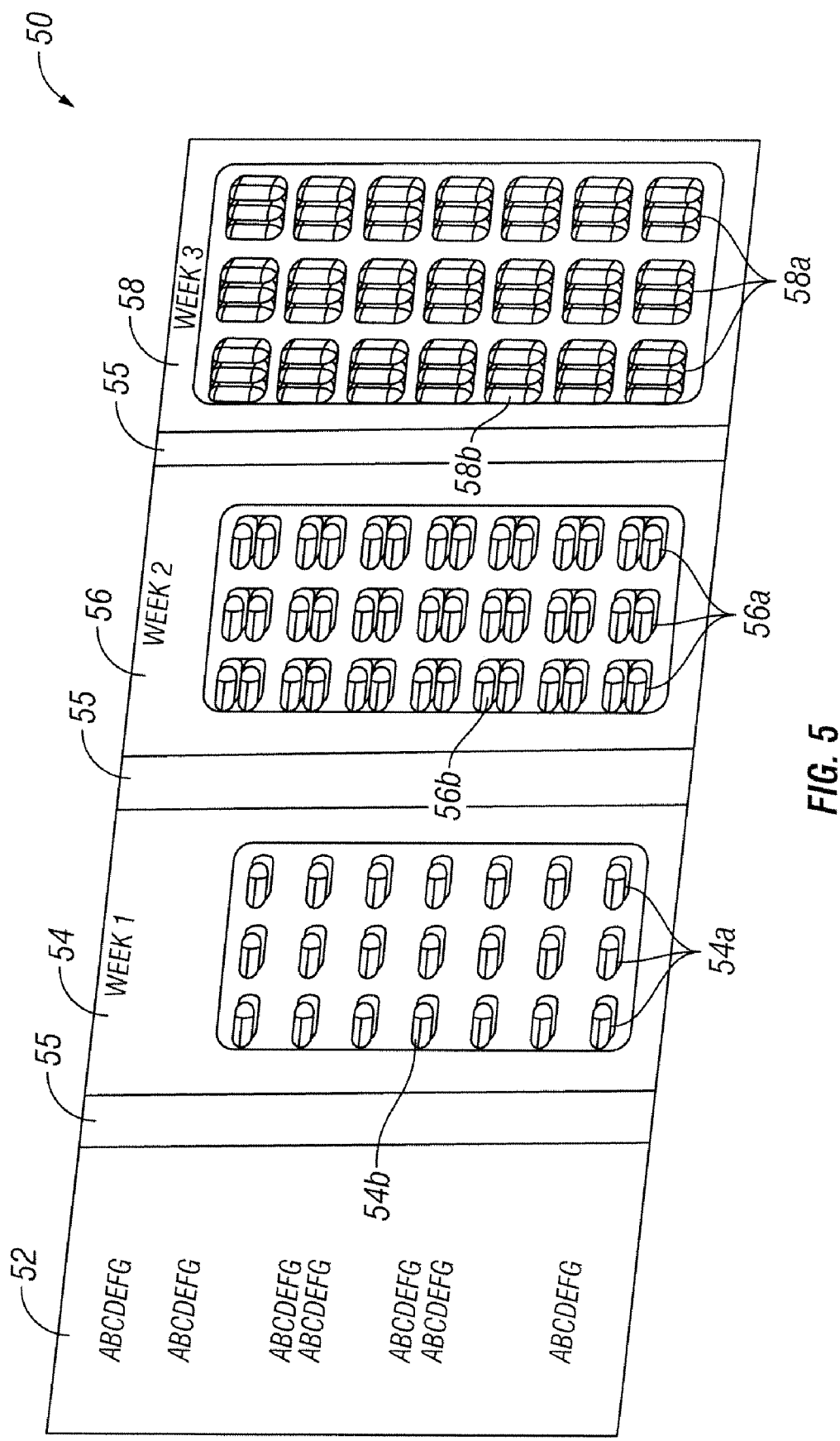
FIG. 5 shows a starter pack having multiple panels in an unfolded position.

FIG. 5 shows a fully unfolded starter pack (50) comprising four panels (52, 54, 56, 58). The Week 1 panel (54) may have compartments (54a) that comprise a dosage amount (54b) of pirfenidone related to the first week of treatment. The Week 2 panel (56) may have compartments (56a) that comprise a dosage amount (56b) of pirfenidone related to the second week of treatment. Optionally, a panel for the dosage amounts of Week 3 may be included. The Week 3 panel (58) may have compartments (58a) that comprise a dosage amount (58b) of pirfenidone related to the third week of usage. The other panel (52) may be left blank or provided with instructions or any other type of indicia. In some embodiments, the starter pack (50) may comprise an adhesive seal or a sticker that holds the starter pack in folded form until the adhesive seal or sticker is broken by a user. The starter pack may comprise regions (55) capable of folding so that the separate panels (52, 54, 56, 58) can be stacked upon one another while the starter pack (50) maintains its unitary structure.

In one embodiment, one panel (54) may comprise compartments (54a) giving the dosage amount (54b) for Days 1-7 of the dose escalation scheme and the second panel (56) may comprise compartments (56a) giving the dosage amount (56b) for Days 8-14 of the dose escalation scheme. In another embodiment, an optional third panel (58) may be further provided to comprise compartments (58a) giving the dosage amount (58b) for Days 15-21 of the dose escalation scheme.

FIG. 6 shows a portion of another starter pack comprising dosage amounts for the first week of therapy using pirfenidone. The starter pack (60) for the first week of treatment may comprise a panel (62) having a plurality of compartments (66) for containing a dosage amount (68) of pirfenidone. The compartments (66) may be arranged in column and row fashion as illustrated, although other arrangements are also contemplated, including having all of the compartments arranged in a line, or having them arranged in a circular fashion. Additionally, instructions may be provided on the starter pack (60) indicating the proper day and time the dosage amount (68) should be administered.

FIG. 7 shows a portion of another starter pack comprising dosage amounts for the second week of therapy using pirfenidone. The starter pack (70) for the second week of treatment may comprise a panel (72) having a plurality of compartments (76) for containing a dosage amount (78) of pirfenidone. The compartments (76) for the second week of treatment may be fashioned to hold a greater amount of pirfenidone than the compartments (66) for the first week of treatment. The dosage amount (78) of pirfenidone for the second week may be greater than the dosage amount (68) of the first week. Additionally, instructions may be provided on the starter pack (70) indicating the proper day and time the dosage amount (78) should be administered.

FIG. 8 shows a portion of another starter pack comprising dosage amounts for the third week of therapy using pirfenidone. The starter pack (80) for the third week of treatment may comprise a panel (82) having a plurality of compartments (86) for containing a dosage amount (88) of pirfenidone. The compartments (86) for the third week of treatment may be fashioned to hold a greater amount of pirfenidone than the compartments (76) for the second week of treatment. The dosage amount (88) of pirfenidone for the third week may be greater than the dosage amount (78) of the second week. Additionally, instructions may be provided on the starter pack (80) indicating the proper day and time the dosage amount (88) should be administered.

Figure 9:
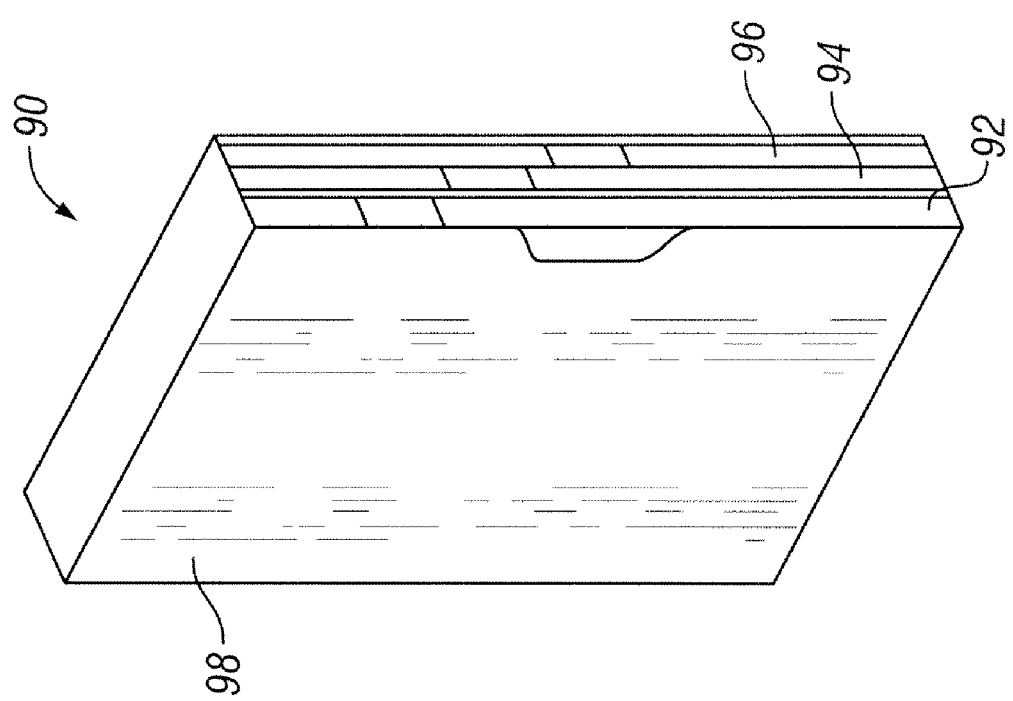
FIG. 9 shows a starter pack having a casing material holding three different containers in such a manner that a user can easily slide a container out of the casing material.

In some embodiments, the starter pack may comprise a casing material that holds separate panels, wherein at least one panel comprises a plurality of compartments for containing a dosage amount of pirfenidone. In some embodiments, the panel may be located within a container having flat outer surfaces so that the container may easily be slid in and out of the casing material. FIG. 9 shows a starter pack (90) having a casing material (98) holding three different containers (92, 94, 96) in such a manner that a user can easily slide a container out of the casing material (98). In one embodiment, each container may comprise a panel that comprises a plurality of compartments that hold a dosage amount of pirfenidone. In some embodiments, the panels may further comprise instructions or indicia so that a user can administer pirfenidone according to the dose escalation scheme. In some embodiments, a panel may be provided separately for providing indicia or instructions on using the drug. In some embodiments, indicia or instructions may be provided on one or more of the containers (92, 94, 96).

Figure 10:
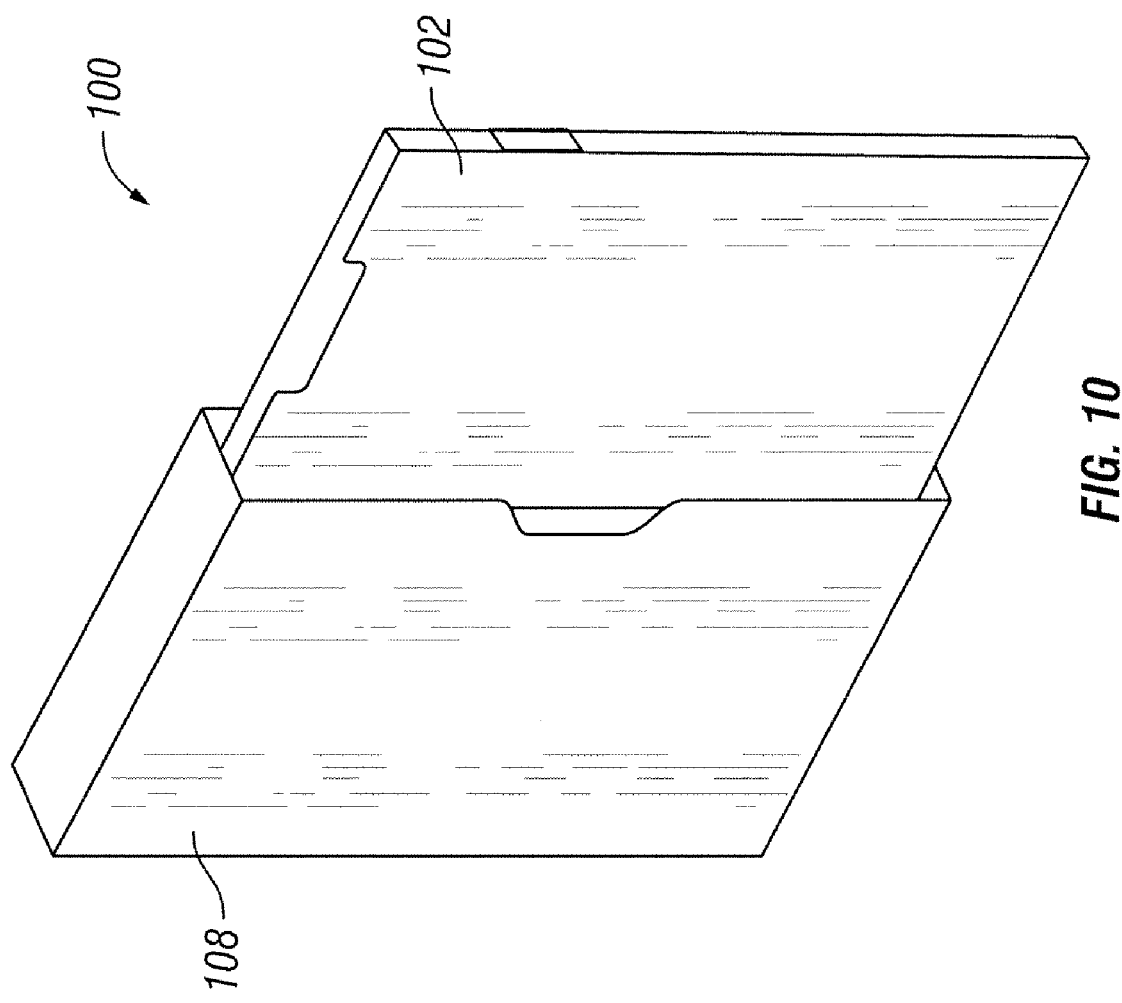
FIG. 10 shows a starter pack wherein a container is partially pulled out from the casing material.

FIG. 10 shows a starter pack (100) comprising a casing material (108) and at least one container (102). The container (102) is partially pulled out from the casing material (108) and may comprise a panel having a plurality of compartments for containing a dosage amount of pirfenidone. For example, the container (102) may comprise any of the panels shown in FIGS. 1-3 and FIGS. 6-8. Preferably, each panel will be approximately the same size for easy and compact insertion into the casing material (108).

Figure 12:
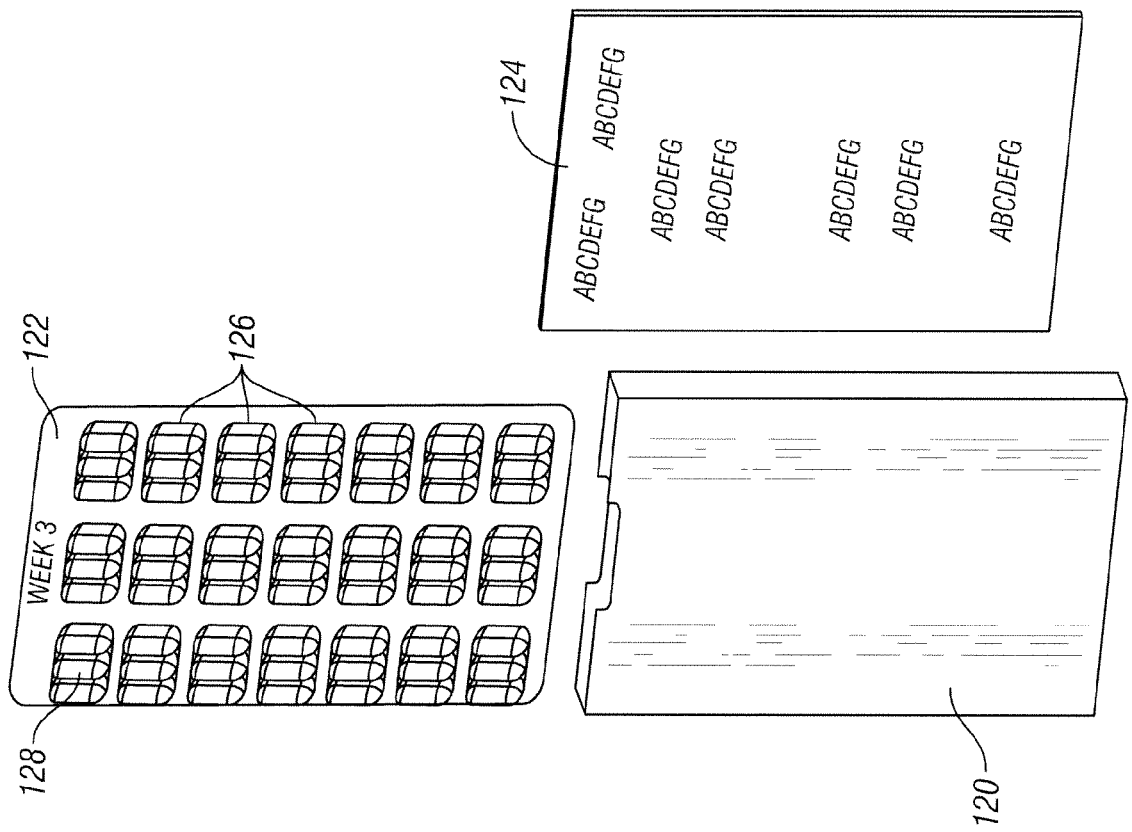
FIG. 12 shows a container wherein the panel has been pulled outside of the container.
Figure 11:
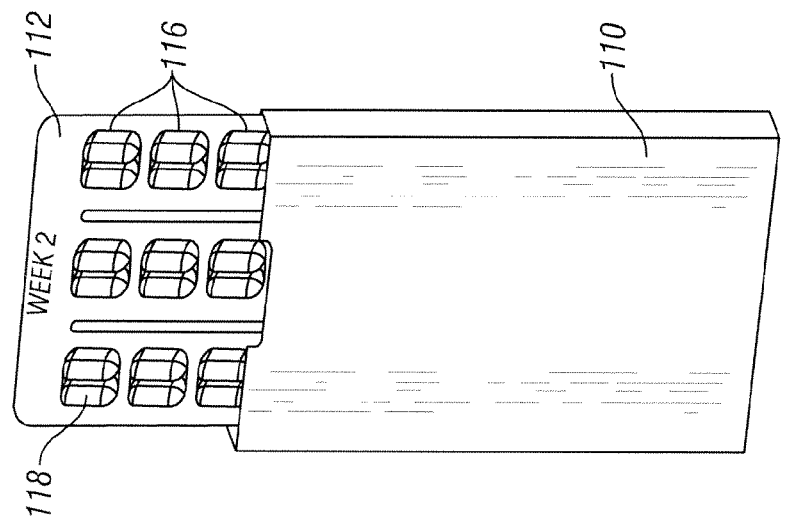
FIG. 11 shows a container comprising a panel having a plurality of compartments for containing a dosage amount of pirfenidone.

FIG. 11 shows a container (110) comprising a panel (112) having a plurality of compartments (116) for containing a dosage amount (118) of pirfenidone. The panel (112) is partially pulled out from the container (110) and can be slid in and out for easy use. FIG. 12 shows a container (120) wherein the panel (122) having a plurality of compartments (126) for containing a dosage amount (128) of pirfenidone has been completely pulled from the container (120). Instructions may be provided on a separate sheet (124) within the container (120) in addition to the panel (122). Alternatively, instructions or other indicia may be printed directly on the container (120) or the panel (122).

One embodiment of the present invention is a starter pack comprising dosage amounts of pirfenidone and compartments that separate the dosage amounts according to a daily dosage of pirfenidone. In one embodiment, the starter pack comprises a row designating Day numbers and separate columns for the number of times a dosage of pirfenidone is taken each day. In one embodiment, the starter pack may comprise separate rows for Days 1, 2, 3, 4, 5, 6, 7, 8, 9, 10, 11, 12, 13, and 14 with three separate columns for three dosage amounts to be taken each day. In one embodiment, each of the three compartments for Days 1, 2, 3, 4, 5, 6, and 7 separately contain one pill of 267-mg pirfenidone and each of the three compartments for Days 8, 9, 10, 11, 12, 13, and 14 separately contain two pills of 267-mg pirfenidone. In another embodiment, each week of treatment may be designated on a separate panel. In another embodiment, each panel contained within the starter pack may be approximately the same size. In another embodiment, the starter pack has compartments arranged such that a user of the starter pack will administer the pirfenidone in accordance with the dose escalation method taught by the present invention.

In one embodiment, the starter pack further comprises additional rows for Days 15, 16, 17, 18, 19, 20, and 21. In another embodiment, each of the three compartments corresponding to Days 15, 16, 17, 18, 19, 20, and 21 separately contain three pills of 267-mg pirfenidone. The addition of the rows for Days 15, 16, 17, 18, 19, 20, and 21 is for the purpose of training the patient as to the correct amount of dosage that will be needed after the starter pack is finished and the patient begins taking pills from another source, such as a pill bottle. By providing the starter pack with a third week at the full dosage of pirfenidone, the patient will be better accustomed to taking the 2,403 mg/day dosage from Day 15 and each Day thereafter as required by the pirfenidone therapy method of the present invention.

In another embodiment, the starter pack comprises a circular form. FIG. 13 shows a container (130) comprising a base (138) that holds at least one panel (132) having a plurality of compartments (136) for containing a dosage amount of pirfenidone. The panel (132) is circular in shape with compartments (136) extending in a radial pattern from the center and wherein each radius designates its own Day for treatment with pirfenidone. The dosages for AM, noon, and PM may be separated in a manner shown in FIG. 13. The container (130) also comprises a lid (139) so that at least one panel (132) containing pirfenidone can be stored within the container (130) and sealed.

FIG. 14 shows a portion of a starter pack comprising dosage amounts for the first week of therapy using pirfenidone. The starter pack (140) for the first week of treatment may comprise a circular panel (142) having a plurality of compartments (146) for containing a dosage amount (148) of pirfenidone. The compartments (146) may be arranged so that they extend radially from the center of the pane (142). The panel (142) may comprise indicia informing the patient which dosage to administer at the appropriate time.

FIG. 15 shows a portion of a starter pack comprising dosage amounts for the second week of therapy using pirfenidone. The starter pack (150) for the second week of treatment may comprise a circular panel (152) having a plurality of compartments (156) for containing a dosage amount (158) of pirfenidone. The compartments (156) may be arranged so that they extend radially from the center or so that they fit within a panel. The panel (152) may comprise indicia informing the patient which dosage to administer at the appropriate time.

FIG. 16 shows a portion of a starter pack comprising dosage amounts for the third week of therapy using pirfenidone. The panel for the third week of therapy is optionally provided. The starter pack (160) for the third week of treatment may comprise a circular panel (162) having a plurality of compartments (166) for containing a dosage amount (168) of pirfenidone. The compartments (146) may be arranged so that they extend radially from the center of the pane (162). The panel (162) may comprise indicia informing the patient which dosage to administer at the appropriate time.

In another embodiment, the starter pack has compartments arranged such that a user of the starter pack will administer the pirfenidone in accordance with the dose escalation method taught by the present invention. Of course, as an alternative to blister packs, the doses can be contained in any other type of compartment, such as plastic bags or other containers fastened together in book form; plastic containers with snap-open lids arranged in a row or other geometric pattern, or any of a wide variety of other dosage-containing packages.

In one embodiment, a method for administering pirfenidone therapy to a patient comprises initially administering a predetermined starting dosage of pirfenidone to the patient and escalating the dosage administered to the patient over a predetermined time to a predetermined full dosage of pirfenidone. In some embodiments, the predetermined time is measured from the initial starting dosage and is between about 7 and 20 days. In some embodiments, the predetermined time is 13 or 14 days. In some embodiments, the starting dosage is about 801 mg/day. In some embodiments, the full dosage is about 2,403 mg/day. In some embodiments, the dosages are split into three daily oral administrations.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention.

What is claimed is:

1. An initial dose escalation regimen method for providing pirfenidone therapy to a patient for the treatment of idiopathic pulmonary fibrosis, comprising:
   providing pirfenidone to a patient at a first oral daily dosage of 801 mg for days one to seven of the dose escalation regimen;
   providing a second oral daily dosage of 1602 mg pirfenidone for days eight to fourteen of the dose escalation regimen; and
   providing a third oral daily dosage of 2403 mg pirfenidone for at least day fifteen of the dose escalation regimen, wherein the patient is provided pirfenidone for the treatment of idiopathic pulmonary fibrosis.

2. The method of claim 1, further comprising instructing the patient to administer the dosage with food.

3. The method of claim 1, wherein each daily dosage is provided as a plurality of dosage forms comprising sub-daily dosages.

4. The method of claim 3, wherein each daily dosage is split into three divided doses provided three times a day.

5. The method of claim 1, wherein each oral daily dosage is provided in capsule form.

6. The method of claim 5, wherein each capsule comprises 267 mg of pirfenidone.

7. A method of reducing the incidence of photosensitivity reaction adverse events in a patient receiving pirfenidone therapy for the treatment of idiopathic pulmonary fibrosis, comprising use of an initial dose escalation regimen comprising the steps of:
   providing pirfenidone to the patient at a first oral daily dosage of 801 mg of pirfenidone for days one to seven of the dose escalation regimen; providing a second oral daily dosage of 1602 mg pirfenidone for days eight to fourteen of the dose escalation regimen; and providing a third oral daily dosage of 2403 mg pirfenidone for at least day fifteen of the dose escalation regimen.

8. The method of claim 7, further comprising instructing the patient to administer the dosage with food.

9. The method of claim 7, wherein each daily dosage is provided as a plurality of dosage forms comprising sub-daily dosages.

10. The method of claim 9, wherein each daily dosage is split into three divided doses provided three times a day.

11. The method of claim 7, wherein each oral daily dosage is provided in capsule form.

12. The method of claim 11, wherein each capsule comprises 267 mg of pirfenidone.

13. In a method of treating a patient with pirfenidone for idiopathic pulmonary fibrosis, the improvement comprising: reducing the incidence of photosensitivity reaction adverse events in the patient receiving pirfenidone therapy by use of an initial dose escalation regimen comprising providing pirfenidone to a patient at a first oral daily dosage of 801 mg of pirfenidone for days one to seven of the dose escalation regimen; providing a second oral daily dosage of 1602 mg pirfenidone for days eight to fourteen of the dose escalation regimen; and providing a third oral daily dosage of 2403 mg pirfenidone for at least day fifteen of the dose escalation regimen.

14. The method of claim 13, further comprising instructing the patient to administer the dosage with food.

15. The method of claim 13, wherein each daily dosage is provided as a plurality of dosage forms comprising sub-daily dosages.

16. The method of claim 15, wherein each daily dosage is split into three divided doses provided three times a day.

17. The method of claim 13, wherein each oral daily dosage is provided in capsule form.

18. The method of claim 17, wherein each capsule comprises 267 mg of pirfenidone.

19. The method of claim 13, comprising reducing the incidence of photosensitivity reaction adverse events to about 12%.

* * * * *